(12) United States Patent
Forster et al.

(10) Patent No.: US 8,142,492 B2
(45) Date of Patent: Mar. 27, 2012

(54) PROSTHETIC VALVE IMPLANTATION SYSTEMS

(75) Inventors: David C. Forster, Los Altos Hills, CA (US); Brian Beckey, Woodside, CA (US); Brandon Walsh, Syracuse, UT (US); Scott Heneveld, Whitmore, CA (US)

(73) Assignee: AorTx, Inc., Redwood City, CA (US)

( * ) Notice: Subject to any disclaimer, the term of this patent is extended or adjusted under 35 U.S.C. 154(b) by 367 days.

(21) Appl. No.: 12/305,624

(22) PCT Filed: Jun. 20, 2007

(86) PCT No.: PCT/US2007/071689
§ 371 (c)(1),
(2), (4) Date: Dec. 18, 2008

(87) PCT Pub. No.: WO2007/149933
PCT Pub. Date: Dec. 27, 2007

(65) Prior Publication Data
US 2009/0228098 A1 Sep. 10, 2009

(51) Int. Cl.
*A61F 2/24* (2006.01)
(52) U.S. Cl. ................ 623/2.18; 623/2.38
(58) Field of Classification Search ............ 623/2.38, 623/2.39, 2.4, 2.41, 2.42, 2.17–2.19, 1.24–1.26
See application file for complete search history.

(56) References Cited

U.S. PATENT DOCUMENTS

| | | | |
|---|---|---|---|
| 1,376,531 A | 1/1888 | Byrnes | |
| 1,314,601 A | 9/1919 | McCaskey | |
| 3,579,642 A | 5/1971 | Hefferman | |
| 3,587,115 A | 6/1971 | Shiley | |
| 3,657,744 A | 4/1972 | Ersek | |
| 3,671,979 A | 6/1972 | Moulopoulos | |
| 3,755,823 A | 9/1973 | Hancock | |
| 3,867,728 A | 2/1975 | Stubstad et al. | |
| 4,056,854 A | 11/1977 | Boretos et al. | |
| 4,106,129 A | 8/1978 | Carpentier et al. | |
| 4,328,839 A | 5/1982 | Lyons et al. | |
| 4,339,831 A | 7/1982 | Johnson | |
| 4,340,091 A | 7/1982 | Skelton et al. | |
| 4,624,822 A | 11/1986 | Arru et al. | |
| 4,683,883 A | 8/1987 | Martin | |
| 4,692,165 A | 9/1987 | Bokros | |
| 4,758,151 A | 7/1988 | Arru et al. | |
| 4,822,345 A | 4/1989 | Danforth | |
| 4,822,353 A | 4/1989 | Bokros | |

(Continued)

FOREIGN PATENT DOCUMENTS

WO     WO 91/17720     11/1991

(Continued)

OTHER PUBLICATIONS

U.S. Appl. No. 11/066,126—Office Action, Oct. 16, 2008.

(Continued)

*Primary Examiner* — Julian Woo
(74) *Attorney, Agent, or Firm* — Dickstein Shapiro LLP; Mark Stirrat (57) ABSTRACT

Prosthetic valves implantation methods and systems, especially as related to fitting a prosthetic valve at the site of a native stenotic or incompetent valve are described. The subject devices, systems and associated dock deployment and implant docking techniques may be employed in percutaneous valve replacement procedures.

25 Claims, 4 Drawing Sheets

U.S. PATENT DOCUMENTS

| | | |
|---|---|---|
| 4,856,516 A | 8/1989 | Hillstead |
| 4,878,495 A | 11/1989 | Grayzel |
| 4,878,906 A | 11/1989 | Lindemann et al. |
| 4,960,424 A | 10/1990 | Grooters |
| 4,994,077 A | 2/1991 | Dobben |
| 5,002,567 A | 3/1991 | Bona et al. |
| 5,037,434 A | 8/1991 | Lane |
| 5,078,737 A | 1/1992 | Bona et al. |
| 5,098,374 A | 3/1992 | Othel-Jacobsen et al. |
| 5,123,919 A | 6/1992 | Sauter et al. |
| 5,163,953 A | 11/1992 | Vince |
| 5,163,954 A | 11/1992 | Curcio et al. |
| 5,213,580 A | 5/1993 | Slepian et al. |
| 5,238,454 A | 8/1993 | Schmidt |
| 5,326,371 A | 7/1994 | Love et al. |
| 5,328,471 A | 7/1994 | Slepian |
| 5,332,402 A * | 7/1994 | Teitelbaum .................. 623/2.42 |
| 5,370,685 A | 12/1994 | Stevens |
| 5,397,348 A | 3/1995 | Campbell et al. |
| 5,397,351 A | 3/1995 | Pavcnik et al. |
| 5,403,305 A | 4/1995 | Sauter et al. |
| 5,411,552 A | 5/1995 | Andersen et al. |
| 5,423,886 A | 6/1995 | Arru et al. |
| 5,443,474 A | 8/1995 | Sfakianos et al. |
| 5,454,838 A | 10/1995 | Vallana et al. |
| 5,522,885 A | 6/1996 | Love et al. |
| 5,531,094 A | 7/1996 | More et al. |
| 5,545,214 A | 8/1996 | Stevens |
| 5,554,185 A | 9/1996 | Block et al. |
| 5,560,487 A | 10/1996 | Starr |
| 5,582,607 A | 12/1996 | Lackman |
| 5,607,442 A | 3/1997 | Fischell et al. |
| 5,620,456 A | 4/1997 | Sauer et al. |
| 5,668,425 A | 9/1997 | Marioni et al. |
| 5,695,515 A | 12/1997 | Orejola |
| 5,713,860 A | 2/1998 | Kaplan et al. |
| 5,713,953 A | 2/1998 | Vallana et al. |
| 5,716,370 A | 2/1998 | Williamson et al. |
| 5,724,705 A | 3/1998 | Hauser et al. |
| 5,772,672 A | 6/1998 | Toy et al. |
| 5,814,097 A | 9/1998 | Sterman et al. |
| 5,823,342 A | 10/1998 | Caudillo et al. |
| 5,840,081 A | 11/1998 | Andersen et al. |
| 5,855,601 A | 1/1999 | Bessler et al. |
| 5,868,708 A | 2/1999 | Hart et al. |
| 5,891,195 A * | 4/1999 | Klostermeyer et al. ...... 623/1.26 |
| 5,919,225 A | 7/1999 | Lau et al. |
| 5,921,993 A | 7/1999 | Yoon |
| 5,925,063 A | 7/1999 | Khosravi |
| 5,957,949 A | 9/1999 | Leonhardt et al. |
| 5,980,570 A | 11/1999 | Simpson |
| 5,984,959 A | 11/1999 | Robertson et al. |
| 6,027,779 A | 2/2000 | Campbell et al. |
| 6,042,607 A | 3/2000 | Williamson, IV et al. |
| 6,051,014 A | 4/2000 | Jang |
| 6,053,922 A | 4/2000 | Krause et al. |
| 6,090,138 A | 7/2000 | Chasak et al. |
| 6,092,529 A | 7/2000 | Cox |
| 6,093,530 A | 7/2000 | McIlroy et al. |
| 6,102,944 A | 8/2000 | Huynh et al. |
| 6,102,945 A | 8/2000 | Campbell |
| 6,117,169 A | 9/2000 | Moe |
| 6,132,986 A | 10/2000 | Pathak et al. |
| 6,143,024 A | 11/2000 | Campbell et al. |
| 6,143,025 A | 11/2000 | Stobie et al. |
| 6,162,172 A | 12/2000 | Cosgrove et al. |
| 6,168,614 B1 | 1/2001 | Andersen et al. |
| 6,174,331 B1 | 1/2001 | Moe et al. |
| 6,182,664 B1 | 2/2001 | Cosgrove |
| 6,197,053 B1 | 3/2001 | Cosgrove et al. |
| 6,199,696 B1 | 3/2001 | Lytle et al. |
| 6,206,918 B1 | 3/2001 | Campbell et al. |
| 6,217,610 B1 | 4/2001 | Carpentier et al. |
| 6,231,578 B1 | 5/2001 | Rajhansa |
| 6,231,602 B1 | 5/2001 | Carpentier et al. |
| 6,241,765 B1 | 6/2001 | Griffin et al. |
| 6,245,102 B1 | 6/2001 | Jayaraman |
| 6,270,526 B1 | 8/2001 | Cox |
| 6,283,995 B1 | 9/2001 | Moe et al. |
| 6,287,339 B1 | 9/2001 | Vazquez et al. |
| 6,299,637 B1 | 10/2001 | Shaolian et al. |
| 6,299,638 B1 | 10/2001 | Sauter |
| 6,338,740 B1 | 1/2002 | Carpentier |
| 6,342,070 B1 | 1/2002 | Nguyen-Thien-Nhon |
| 6,348,068 B1 | 2/2002 | Campbell et al. |
| 6,350,281 B1 | 2/2002 | Rhee |
| 6,350,732 B1 | 2/2002 | Moore et al. |
| 6,364,905 B1 | 4/2002 | Simpson et al. |
| 6,371,983 B1 | 4/2002 | Lane |
| 6,383,147 B1 | 5/2002 | Stobie |
| 6,391,054 B2 | 5/2002 | Carpentier et al. |
| 6,402,780 B2 | 6/2002 | Williamson, IV et al. |
| 6,405,084 B2 | 6/2002 | Plicchi et al. |
| 6,409,758 B2 | 6/2002 | Stobie et al. |
| 6,425,916 B1 | 7/2002 | Garrison et al. |
| 6,453,062 B1 | 9/2002 | MacNutt et al. |
| 6,454,799 B1 * | 9/2002 | Schreck ...................... 623/2.18 |
| 6,458,155 B1 | 10/2002 | Van Nguyen et al. |
| 6,461,382 B1 | 10/2002 | Cao |
| 6,475,239 B1 | 11/2002 | Campbell et al. |
| 6,479,079 B1 | 11/2002 | Pathak et al. |
| 6,482,228 B1 | 11/2002 | Norred |
| 6,485,512 B1 | 11/2002 | Cheng |
| 6,493,585 B2 | 12/2002 | Plicchi et al. |
| 6,530,952 B2 | 3/2003 | Vesely |
| 6,544,279 B1 | 4/2003 | Hopkins et al. |
| 6,558,418 B2 | 5/2003 | Carpentier et al. |
| 6,565,602 B2 | 5/2003 | Rolando et al. |
| 6,569,196 B1 | 5/2003 | Vesely |
| 6,572,642 B2 | 6/2003 | Rinaldi et al. |
| 6,582,462 B1 | 6/2003 | Andersen et al. |
| 6,585,632 B2 | 7/2003 | Vallana et al. |
| 6,585,766 B1 | 7/2003 | Huynh et al. |
| 6,596,471 B2 | 7/2003 | Pathak et al. |
| 6,602,288 B1 | 8/2003 | Cosgrove et al. |
| 6,613,085 B1 | 9/2003 | Anderson et al. |
| 6,616,690 B2 | 9/2003 | Rolando et al. |
| 6,635,085 B1 | 10/2003 | Caffey et al. |
| 6,638,303 B1 | 10/2003 | Campbell |
| 6,652,578 B2 | 11/2003 | Bailey et al. |
| 6,663,667 B2 | 12/2003 | Dehdashtian et al. |
| 6,673,109 B2 | 1/2004 | Cox |
| 6,679,871 B2 | 1/2004 | Hahnen |
| 6,682,543 B2 | 1/2004 | Barbut et al. |
| 6,682,558 B2 | 1/2004 | Tu et al. |
| 6,682,559 B2 | 1/2004 | Myers et al. |
| 6,689,149 B2 | 2/2004 | Maahs |
| 6,692,512 B2 | 2/2004 | Jang |
| 6,706,033 B1 | 3/2004 | Martinez et al. |
| 6,719,787 B2 | 4/2004 | Cox |
| 6,719,788 B2 | 4/2004 | Cox |
| 6,719,789 B2 | 4/2004 | Cox |
| 6,723,122 B2 | 4/2004 | Yang et al. |
| 6,730,118 B2 | 5/2004 | Spenser et al. |
| 6,733,513 B2 | 5/2004 | Boyle et al. |
| 6,733,525 B2 | 5/2004 | Yang et al. |
| 6,736,845 B2 | 5/2004 | Marquez et al. |
| 6,736,846 B2 | 5/2004 | Cox |
| 6,767,362 B2 | 7/2004 | Schreck |
| 6,770,083 B2 | 8/2004 | Seguin |
| 6,783,988 B1 | 8/2004 | Dinh et al. |
| 6,790,219 B1 | 9/2004 | Murphy |
| 6,796,972 B1 | 9/2004 | Sinofsky et al. |
| 6,797,000 B2 | 9/2004 | Simpson et al. |
| 6,805,710 B2 | 10/2004 | Bolling et al. |
| 6,821,279 B2 | 11/2004 | Di Emidio |
| 6,821,297 B2 | 11/2004 | Snyders |
| 6,846,324 B2 | 1/2005 | Stobie |
| 6,849,088 B2 | 2/2005 | Dehdashtian et al. |
| 6,858,039 B2 | 2/2005 | McCarthy |
| 6,875,231 B2 | 4/2005 | Anduiza et al. |
| 6,878,168 B2 | 4/2005 | Carpentier et al. |
| 6,893,460 B2 | 5/2005 | Spenser et al. |
| 6,896,698 B2 | 5/2005 | Rolando et al. |
| 6,908,481 B2 | 6/2005 | Cribier |
| 6,939,365 B1 | 9/2005 | Fogarty et al. |
| 6,945,997 B2 | 9/2005 | Huynh et al. |

| | | |
|---|---|---|
| 6,951,571 B1 | 10/2005 | Srivastava |
| 6,962,605 B2 | 11/2005 | Cosgrove et al. |
| 6,986,775 B2 | 1/2006 | Morales et al. |
| 6,988,881 B2 | 1/2006 | Motsenbocker et al. |
| 6,989,028 B2 | 1/2006 | Lashinski et al. |
| 7,004,176 B2 | 2/2006 | Lau |
| 7,011,669 B2 | 3/2006 | Kimblad |
| 7,011,681 B2 | 3/2006 | Vesely |
| 7,011,682 B2 | 3/2006 | Lashinski et al. |
| 7,014,648 B2 | 3/2006 | Ambrisco et al. |
| 7,018,406 B2 | 3/2006 | Seguin et al. |
| 7,060,092 B2 | 6/2006 | Kuribayashi et al. |
| 7,252,682 B2 | 8/2007 | Seguin |
| 7,374,571 B2 | 5/2008 | Pease et al. |
| 7,429,270 B2 | 9/2008 | Baumgartner et al. |
| 7,967,857 B2 * | 6/2011 | Lane .................... 623/2.38 |
| 2001/0016758 A1 | 8/2001 | Plicchi et al. |
| 2001/0018600 A1 | 8/2001 | Plicchi et al. |
| 2001/0039450 A1 | 11/2001 | Pavcnik et al. |
| 2001/0049541 A1 | 12/2001 | Plicchi et al. |
| 2002/0032482 A1 | 3/2002 | Cox |
| 2002/0038128 A1 | 3/2002 | Turovkiy et al. |
| 2002/0042651 A1 | 4/2002 | Liddicoat et al. |
| 2002/0052647 A1 | 5/2002 | Rolando et al. |
| 2002/0055775 A1 | 5/2002 | Carpentier et al. |
| 2002/0058994 A1 | 5/2002 | Hill et al. |
| 2002/0072793 A1 | 6/2002 | Rolando et al. |
| 2002/0095173 A1 | 7/2002 | Mazzocchi et al. |
| 2002/0099441 A1 | 7/2002 | Dehdashtian |
| 2002/0117264 A1 | 8/2002 | Rinaldi et al. |
| 2002/0133226 A1 | 9/2002 | Marquez et al. |
| 2002/0138138 A1 | 9/2002 | Yang |
| 2002/0161431 A1 | 10/2002 | Stobie et al. |
| 2002/0163104 A1 | 11/2002 | Motsenbocker et al. |
| 2002/0183766 A1 | 12/2002 | Seguin |
| 2002/0183831 A1 | 12/2002 | Rolando et al. |
| 2003/0009076 A1 | 1/2003 | Vallana et al. |
| 2003/0023262 A1 | 1/2003 | Welch |
| 2003/0027332 A1 | 2/2003 | Lafrance et al. |
| 2003/0033002 A1 | 2/2003 | Dehdashtian et al. |
| 2003/0036795 A1 | 2/2003 | Andersen et al. |
| 2003/0050694 A1 | 3/2003 | Yang et al. |
| 2003/0055495 A1 | 3/2003 | Pease et al. |
| 2003/0065356 A1 | 4/2003 | Tsugita et al. |
| 2003/0114913 A1 | 6/2003 | Spenser et al. |
| 2003/0114917 A1 | 6/2003 | Holloway et al. |
| 2003/0130721 A1 | 7/2003 | Martin et al. |
| 2003/0153943 A1 | 8/2003 | Michael et al. |
| 2003/0153946 A1 | 8/2003 | Kimblad |
| 2003/0195613 A1 | 10/2003 | Curcio et al. |
| 2003/0212433 A1 | 11/2003 | Ambrisco et al. |
| 2004/0015224 A1 | 1/2004 | Armstrong et al. |
| 2004/0030382 A1 | 2/2004 | St. Goar et al. |
| 2004/0034380 A1 | 2/2004 | Woolfson et al. |
| 2004/0049266 A1 | 3/2004 | Anduiza et al. |
| 2004/0078074 A1 | 4/2004 | Anderson et al. |
| 2004/0092858 A1 | 5/2004 | Wilson et al. |
| 2004/0092989 A1 | 5/2004 | Wilson et al. |
| 2004/0093060 A1 | 5/2004 | Seguin et al. |
| 2004/0093080 A1 | 5/2004 | Helmus et al. |
| 2004/0127979 A1 | 7/2004 | Wilson et al. |
| 2004/0148017 A1 | 7/2004 | Stobie |
| 2004/0148018 A1 | 7/2004 | Carpentier et al. |
| 2004/0153140 A1 | 8/2004 | Rolando et al. |
| 2004/0158276 A1 | 8/2004 | Barbut et al. |
| 2004/0172124 A1 | 9/2004 | Vallana et al. |
| 2004/0186563 A1 | 9/2004 | Lobbi |
| 2004/0199245 A1 | 10/2004 | Lauterjung |
| 2004/0210304 A1 | 10/2004 | Seguin et al. |
| 2004/0225352 A1 | 11/2004 | Osborne et al. |
| 2004/0243222 A1 | 12/2004 | Osborne et al. |
| 2004/0249433 A1 | 12/2004 | Freitag |
| 2005/0027337 A1 | 2/2005 | Rudko et al. |
| 2005/0033398 A1 | 2/2005 | Seguin |
| 2005/0038497 A1 | 2/2005 | Neuendorf et al. |
| 2005/0043760 A1 | 2/2005 | Fogarty et al. |
| 2005/0043790 A1 | 2/2005 | Seguin |
| 2005/0043792 A1 | 2/2005 | Solem et al. |
| 2005/0065594 A1 | 3/2005 | DiMatteo et al. |
| 2005/0075584 A1 | 4/2005 | Cali |
| 2005/0075712 A1 | 4/2005 | Biancucci et al. |
| 2005/0075725 A1 | 4/2005 | Rowe |
| 2005/0090888 A1 | 4/2005 | Hines et al. |
| 2005/0096734 A1 | 5/2005 | Majercak et al. |
| 2005/0096740 A1 | 5/2005 | Langberg et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137696 A1 | 6/2005 | Salahieh et al. |
| 2005/0137699 A1 | 6/2005 | Salahieh et al. |
| 2005/0137701 A1 | 6/2005 | Salahieh et al. |
| 2005/0143809 A1 | 6/2005 | Salahieh et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0228485 A1 | 10/2005 | Rolando et al. |
| 2005/0228495 A1 | 10/2005 | Macoviak |
| 2005/0267493 A1 | 12/2005 | Schreck et al. |
| 2005/0277959 A1 | 12/2005 | Cosgrove et al. |
| 2006/0004442 A1 | 1/2006 | Spenser et al. |
| 2006/0015179 A1 | 1/2006 | Bulman-Fleming et al. |
| 2006/0025787 A1 | 2/2006 | Morales et al. |
| 2006/0025854 A1 | 2/2006 | Lashinski et al. |
| 2006/0025855 A1 | 2/2006 | Lashinski et al. |
| 2006/0052867 A1 | 3/2006 | Revuelta |
| 2006/0058871 A1 | 3/2006 | Zakay et al. |
| 2006/0069424 A1 | 3/2006 | Acosta et al. |
| 2006/0095052 A1 | 5/2006 | Chambers |
| 2006/0122633 A1 | 6/2006 | To et al. |
| 2006/0173537 A1 | 8/2006 | Yang et al. |
| 2006/0217764 A1 | 9/2006 | Abbott et al. |
| 2007/0016286 A1 | 1/2007 | Herrmann et al. |
| 2007/0088431 A1 | 4/2007 | Bourang et al. |
| 2008/0140172 A1 | 6/2008 | Carpenter et al. |

FOREIGN PATENT DOCUMENTS

| | | |
|---|---|---|
| WO | WO 99/33414 | 7/1999 |
| WO | WO 01/76510 A2 | 10/2001 |
| WO | WO 03/003949 A2 | 1/2003 |
| WO | WO 03/047468 A1 | 6/2003 |
| WO | WO 03/096932 A | 11/2003 |
| WO | WO 03/105670 A2 | 12/2003 |
| WO | WO 2005009285 A2 | 2/2005 |
| WO | WO 2005/076973 A2 | 8/2005 |
| WO | WO 2005/087140 A1 | 9/2005 |
| WO | WO 2006/066150 A2 | 6/2006 |

OTHER PUBLICATIONS

U.S. Appl. No. 11/066,126—Office Action, Apr. 3, 2009.
U.S. Appl. No. 11/066,126—Office Action, Dec. 22, 2009.
U.S. Appl. No. 11/066,124—Office Action, Mar. 7, 2007.
U.S. Appl. No. 11/066,124—Office Action, Mar. 7, 2008.
U.S. Appl. No. 11/066,124—Office Action, Oct. 2, 2008.
U.S. Appl. No. 11/066,124—Office Action, Jun. 9, 2009.
U.S. Appl. No. 11/067,330—Office Action, Apr. 16, 2007.
U.S. Appl. No. 11/067,330—Office Action, Jun. 11, 2008.
U.S. Appl. No. 11/067,330—Office Action, Jun. 10, 2009.
U.S. Appl. No. 11/364,715—Office Action, Dec. 11, 2006.
U.S. Appl. No. 11/364,715—Office Action, Oct. 18, 2007.
U.S. Appl. No. 11/364,715—Office Action, Jan. 12, 2009.
CN Ser. No. 200580012735.5—Office Action, Jan. 9, 2009.
CN Ser. No. 200580012735.5—Office Action, Jul. 10, 2009.
EP Ser. No. 05723873.5—ESR, Nov. 3, 2009.
WO Ser. No. WO2007/101159—ISR, Apr. 24, 2008.
WO Ser. No. WO2007/101160—ISR, Dec. 11, 2007.

WO Ser. No. WO2007/149905—ISR, Aug. 29, 2008.
WO Ser. No. WO2007/149841—ISR, Jul. 30, 2008.
WO Ser. No. WO2007/149933—ISR, Aug. 15, 2008.
WO Ser. No. WO2007/149910—ISR, Jan. 28, 2008.
WO Ser. No. WO2008/030946—ISR, Jan. 11, 2008.
EP, European Search Report, Appln. No. 07798835.0-2320, Mar. 2, 2010.
EP, European Search Report, Appln. No. 07757493.7-2320, Mar. 15, 2010.
EP, European Search Report, Appln. No. 07798822.2-2320, Mar. 8, 2010.
EP, European Search Report, Appln. No. 07814809.9-2320, Mar. 3, 2010.

* cited by examiner

PROSTHETIC VALVE IMPLANTATION SYSTEMS

BACKGROUND OF THE INVENTION

Diseases and other disorders of the heart valves affect the proper flow of blood from the heart. Two categories of heart valve disease are stenosis and incompetence. Stenosis refers to a failure of the valve to open fully, due to stiffened valve tissue. Incompetence refers to valves that cause inefficient blood circulation by permitting backflow of blood in the heart.

Medication may be used to treat some heart valve disorders, but many cases require replacement of the native valve with a prosthetic heart valve. Prosthetic heart valves can be used to replace any of the native heart valves (aortic, mitral, tricuspid or pulmonary), although repair or replacement of the aortic or mitral valves is most common because they reside in the left side of the heart where pressures are the greatest.

Conventional heart valve replacement surgery involves accessing the heart in the patent's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass support which involves stopping the heart to permit access to the internal chambers. Such open heart surgery is particularly invasive and involves a lengthy and difficult recovery period.

Figures 1A, 1B:
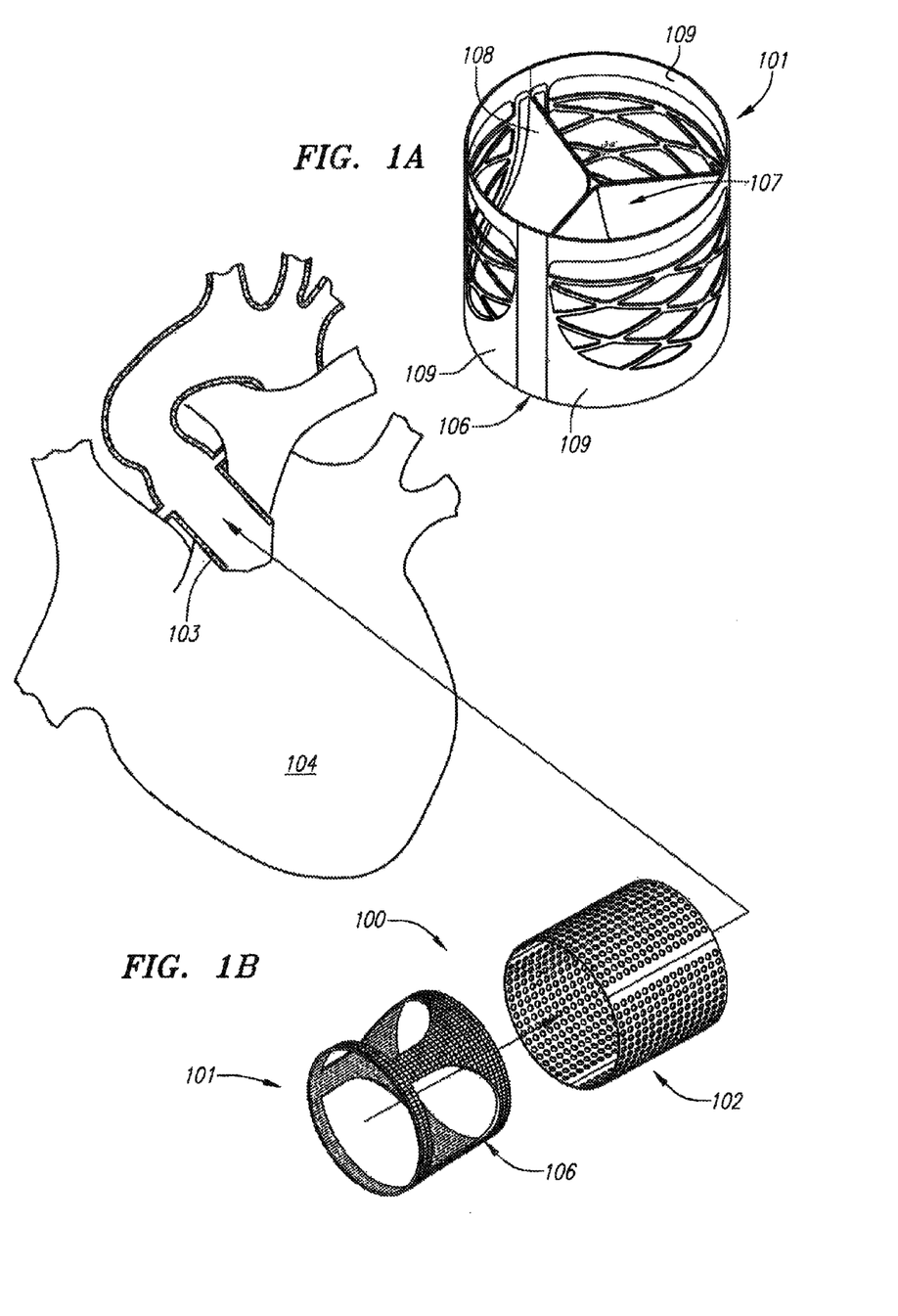
FIG. 1A is a perspective view depicting an exemplary valve prosthesis.
FIG. 1B is an illustrative view depicting an exemplary embodiment of a docking system drawing relation to a heart.

Percutaneous implantation of a prosthetic valve is a preferred procedure because the operation is performed under local anesthesia, may not require cardiopulmonary bypass, and is less traumatic. Various types of prosthetics are adapted for such use. One class employs a stent like outer body and internal valve leaflets attached thereto to provide one way blood flow. These stent structures are radially contracted for delivery to the intended site, and then expanded/deployed to achieve a tubular structure in the annulus. Another more advantageous class is offered by the assignee hereof. US Patent Publication No. 2005/0203614 (hereinafter "the '614 application," which application is incorporated by reference herein in its entirety) describes a system in which various panels define the implant body carrying valve leaflets. These prosthetic valve structures are delivered in a contracted state and then unfolded and/or unrolled into an expanded state at the treatment location. An example of such a valve is depicted in FIG. 1A. As shown, valve prosthesis 101 is adapted to carry a valve 107 having multiple leaflets 108. The valve support structure 106 includes a plurality of panels 109 that can transition from the state shown to an inverted state as described in the '614 publication.

With either type of structure, a sufficient engagement between patient body tissue and the prosthesis body is desired to secure the position of the implant and form a peripheral seal. However, when implanting the prosthetic device at the site of/within the envelope of the native valve, the condition of the native valve can interfere with fit. Stated otherwise, irregularity in the shape of the implantation site, surface features, texture, and composition pose challenges for developing an implant of a regular size able to accommodate all such variability.

Aspects of the invention optionally address the challenges presented by prosthetic member interface with calcific and/or irregular valve leaflet and annulus geometry. In addition, other advantages of the present invention may be apparent to those with skill in the art upon review of the subject disclosure.

BRIEF SUMMARY OF THE INVENTION

This summary is provided by way of exemplary embodiments. In no way is this summary intended to provide limitation to the scope of the appended claims.

Accordingly, the systems and methods described herein include "docking" type devices for interfacing with replacement prosthetic valves. In some exemplary embodiments, these docking devices are in the form of a sleeve adapted to secure a valve body within a central lumen, and interface with native tissue around its periphery. The docking sleeves can be adapted to provide a seal between the native valve or vessel and the valve body.

BRIEF DESCRIPTION OF THE DRAWINGS

The figures provided herein are not necessarily drawn to scale, with some components and features being exaggerated for clarity. Each of the figures diagrammatically illustrates aspects of the invention. Variation of the invention from the embodiments pictured is contemplated.

DETAILED DESCRIPTION OF THE INVENTION

As opposed to known systems, an aspect of the systems and methods described herein contemplates more than a simple docking ring with a limited implant-retention interface. In the systems and methods described herein, the sleeve is adapted to receive at least half, and more typically the entire valve body. Such overlap provides for valve/sleeve interface or securing approaches elaborated upon below. FIG. 1B is a illustrative view depicting a docking system 100 having a support structure 106 of a valve prosthesis 101 as described in the '614 publication and a corresponding docking sleeve 102 adapted to receive valve support structure 106. Placement of the docking sleeve 102 can occur in a location corresponding to the presence of a native valve, such as the aortic valve within the aorta 103 of the heart 104 of a patient.

Another aspect of the systems and methods described herein that distinguish them from known stent-like and simple stent-graft docking structures is that the sleeves described herein offer a space-filling function to provide each of a good interface with irregular anatomy and a central lumen having a regular shape (e.g., circular, oval or elliptical) to accommodate corresponding valve body geometry. Stated otherwise, docking sleeves are provide that adapt to or take-up space and/or compress or expand in sections to provide a superior vessel-side interface while offering an inner lumen with more regular geometry than the implantation site for valve body retention.

Figure 2A:
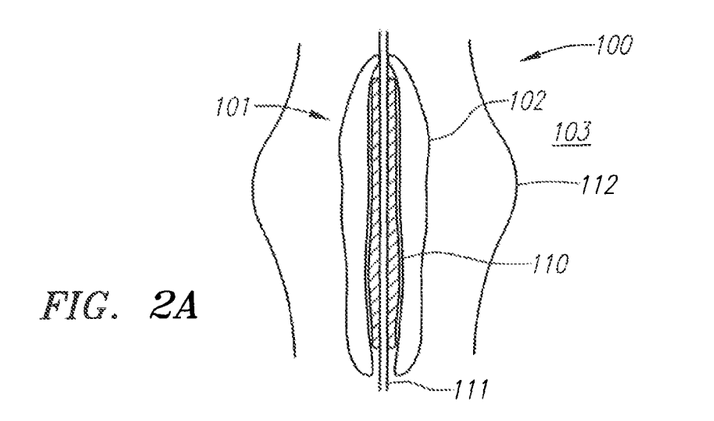
FIGS. 2A-C are cross-sectional views depicting an exemplary embodiment of a docking system 100.
Figure 2B:
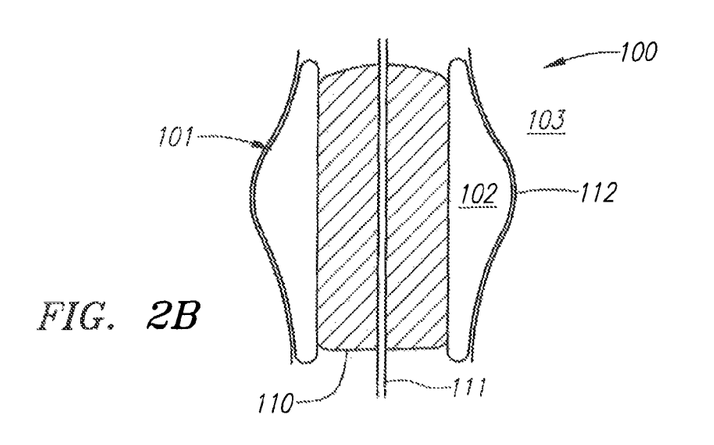
Figure 2C:
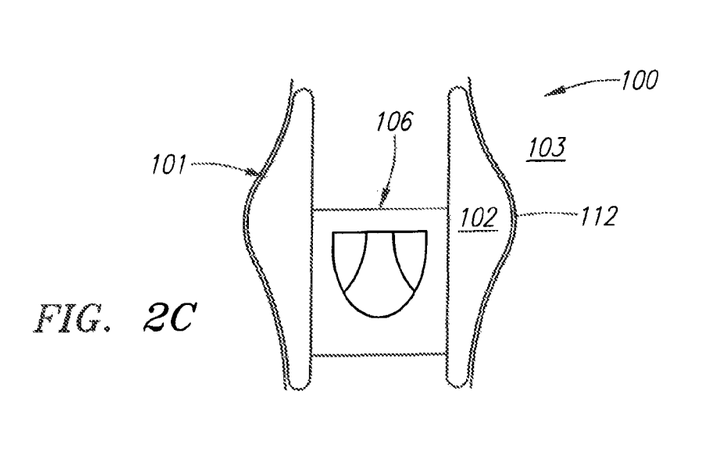

FIGS. 2A-C are cross-sectional views depicting an exemplary embodiment of a prosthesis 101 during various stages of deployment within aorta 103. In this embodiment, docking sleeve 102 is configured as a tissue graft with a variable thickness to conform to the underlying vessel anatomy (in this example, within aorta 103). Of course, in other embodiments, docking sleeve 102 can be composed of man-made materials and/or can be configured in a manner that does not enact full conformation with the underlying anatomy. FIG. 2A depicts graft 102 carried on an expandable member (e.g., a balloon) 110 in its unexpanded state disposed on an elongate member (e.g., a catheter shaft) 111. FIG. 2B depicts graft 102 in a deployed configuration against the walls of aorta 103 and filling sinus 112. The deployment of graft 102 is accomplished by inflation of balloon 110. FIG. 2C depicts graft 102 following the removal of balloon 110 and shaft 111 and the deployment of valve structure 106 (leaflets not shown). Here, it can be seen that structure 106 has a lesser length that graft 102, allowing greater freedom in the placement of structure 106. Also, graft 102 provides space-filling conformance with the underlying anatomy.

Such space-filling may be provided by a compliant body or body portion (e.g., biocompatible "spongy" foam such as expanded PTFE deflectable panels or leaf springs for a metallic material such as NiTi, a microporous polymer or metal/metal alloy, etc.), a multi-component/segment or composite body, or a body with a rigid implant-interface lumen and expandable exterior (e.g., as provided by a hydrogel, or permanently inflatable structure—via air, saline or another biocompatible fluid).

For a multi-component sleeve body, inner and outer tubular (e.g., cylindrical) sections may be provided with a spring media provided therebetween. Multiple elastomeric beams or metal spring (coil, torsion, zig-zag, etc.) elements may be employed for such purposes. Alternatively, an air-spring approach with an interposed balloon (distensible or non-distensible) may be utilized. In the latter case, no additional seal element is required between the inner and outer sleeve housings. However, in the former case, one or more baffle structures (e.g. provided by woven fabric/fiber) may be employed to seal the body from inadvertent blood flow or passage/leakage. In order to avoid inadvertently supplying a cavity prone to thrombus formation, multi-piece sleeve bodies will typically be sealed-off at both ends.

Figure 3A:
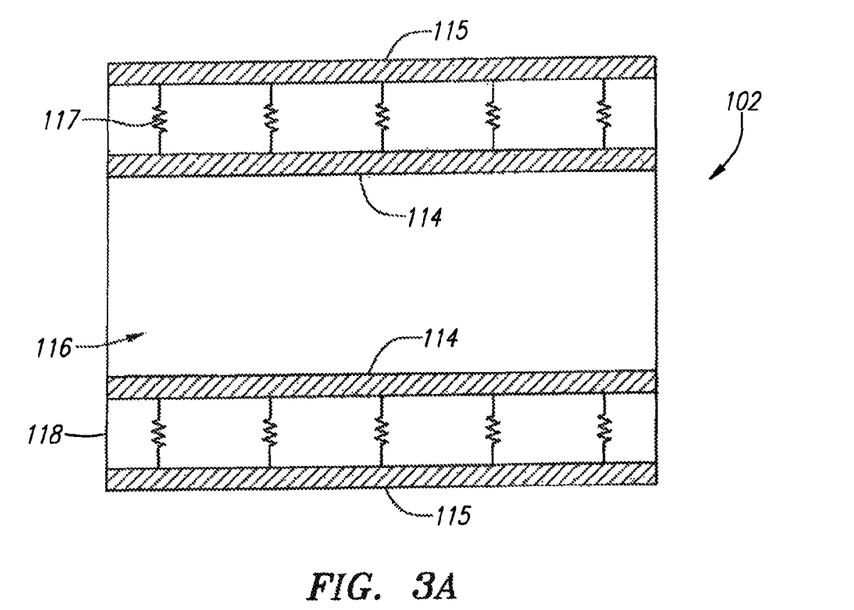
FIGS. 3A-B are axial and radial cross-sectional views, respectively, depicting additional exemplary embodiments of docking sleeve.

FIGS. 3A-B are axial and radial cross-sectional views, respectively, depicting additional exemplary embodiments of docking sleeve 102 having an inner sleeve 114 and an outer sleeve 115. In FIG. 3A, inner sleeve 114 (which can also be valve support structure 106) and outer sleeve 115 are in spaced relation to each other in the deployed configuration with multiple spring elements 117, which are coiled springs in this embodiment, located and exerting force between the outer surface of inner sleeve 114 and the inner surface of outer sleeve 115. Spring elements 118 serve to provide conformance to the underlying anatomy as well as to center inner sleeve 114 with respect to outer sleeve 115. Empty region 116 is configured to receive valve support structure 106 (not shown). Covering 118, which is a flexible fabric in this embodiment, is placed over the gap between sleeves 114 and 115 to seal the region therebetween from blood flow.

Figure 3B:
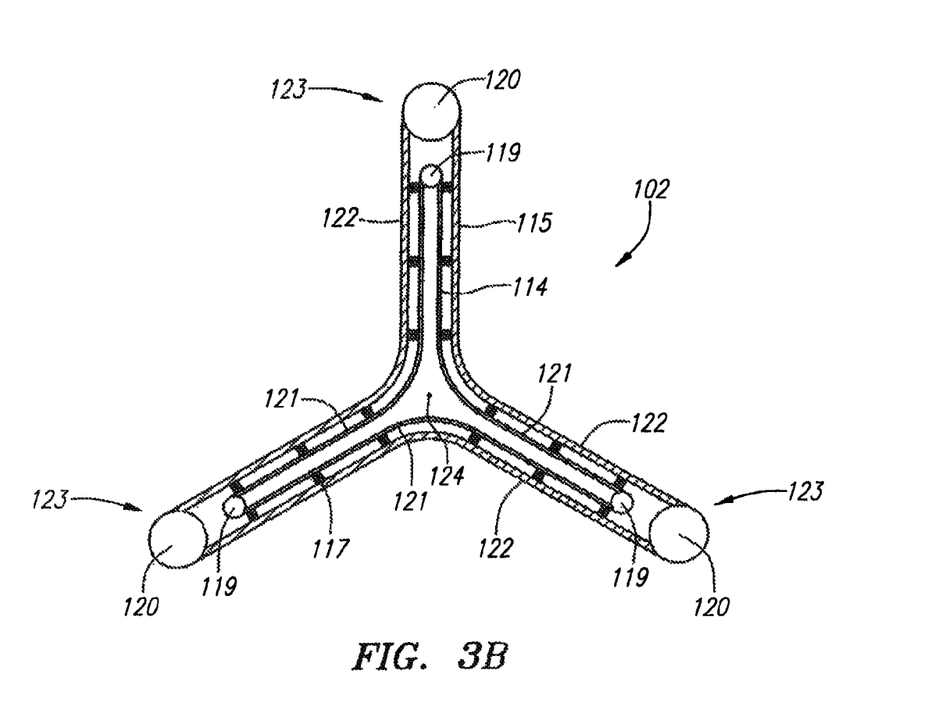

In FIG. 3B, docking sleeve 102 is shown in an exemplary intermediate undeployed configuration. Here, sleeves 114 and 115 are in a "tri-star" configuration similar to that described in the incorporated '614 application. Here, device 102 has three segments 123 arranged in a star-like manner. From this configuration, the profile of the device to be reduced further by rolling each segment towards the center axis 124. Sleeves 114 and 115 can be made to enter this configuration by inverting or deflecting each of panels 121 and 122, respectively, towards the center axis 124 of the device in a manner similar to that described in the '614 application. Hinges 119 and 120 are included between panels 121 and 122, respectively, to facilitate transition between the tri-star and deployed configurations. Although spring elements 117 can also be seen, covering 118 is not shown for clarity.

The length of the sleeve may vary as alluded to above. In order to bridge irregular anatomy such as the aortic sinus, the docking sleeve may be elongated relative to the valve body.

In a procedure for implanting a docking sleeve and prosthetic valve according to the present invention, various tissue modification techniques as described in commonly assigned, "Prosthetic Valve Implant Site Preparation Techniques," provisional application Ser. No. 60/805,333, filed on Jun. 20, 2006 and incorporated by reference in its entirety, can be performed. However, in many instances, the current invention will allow foregoing approach without ill effect.

In one variation of the invention, a method is provided in which the docking sleeve is situated where its implantation is desired during a valvuloplasty procedure. After crossing the native valve leaflets, a balloon is expanded to simultaneously open the leaflets and deploy the docking sleeve.

In order that the interfacing valve is readily available to complete the procedure without compromising patient hemodynamics for an extended period during a beating heart procedure (given that the native valve leaflets are pinned behind the docking sleeve), the valve delivery device may also already be positioned in the aorta for immediate valve body insertion following docking sleeve or station deployment. Such a situation is facilitated by accessing the femoral artery in each leg of a patient to feed the different implant delivery systems (one from the right, and one from the left) into the aortic arch where there is sufficient room to accommodate both.

Alternatively, a temporary valve structure such as described in US Publication No. 2004/0225354 may be provided to allow advancement and delivery of the sleeve, withdrawal of its delivery catheter or guide and substitution for a valve body delivery guide for secondary implant delivery. US Publication No. 2001/0044591 discloses other approaches for percutaneous implant delivery that may alternatively be employed for delivering the docking sleeve and valve body.

As described above, the docking sleeve may be delivered upon a balloon—similar to delivery of a graft. In other variations where the implant comprises a plurality of flexible and/or hinged panels, it may be delivered in a fashion identical to the approach to valve body delivery described directly below.

Specifically, in delivering a prosthetic valve assembly as described in US Publication No. 2005/0203614, after advancing the subject delivery system over the guidewire to the treatment location, its outer sheath is retracted to expose the delivery tube. The gripper provided is then rotated relative to the delivery tube (or the delivery tube rotated relative to the gripper) to cause folded segments of the prosthetic valve to uncurl and to extend radially outward through longitudinal slots of the delivery tube. The delivery tube is then retracted (or the gripper advanced) to cause the prosthetic valve (restrained by the fingers) to advance distally out of the delivery tube. The gripper is then retracted relative to the prosthetic valve, releasing the prosthetic valve into the treatment location. Preferably, the inverted segments then revert to the expanded state, causing the valve to lodge against the internal surface of the body lumen (e.g., the aortic valve root or another biologically acceptable aortic position). Additional expansion of the prosthetic valve may be provided, if needed, by a suitable expansion member, such as an expansion balloon or an expanding mesh member (described elsewhere herein), carried on the delivery catheter or other carrier.

In other methods, different types of prosthetic valves are delivered and deployed within the docking sleeve. In any case, either the valve body or the lumen of the docking sleeve (or both) may be specially adapted to provide a secure interface between the members. Such adaptation may involve complementary VELCRO type hooks, protrusions, tines and loops, dimples, lattice spaces and/or cutouts. Otherwise, a frictional type interface or an interference fit may hold the bodies together. Another means for securing the relative position of the members involves magnets. A plurality of discrete magnetic and/or ferromagnetic elements may be provided. Otherwise, one or both members may be at least partially constructed with magnetic impregnated material (such as polymeric sheet).

Common to all of the approaches, in accordance with another possibly independent aspect of the invention, is the manner in which a large portion or the entirety of the axial length of the implant is engaged with the docking sleeve. The preferred valve body variations have an axial length in which the valve leaflets are set. These "high walls" may help protect the leaflets (especially when closed-wall valve body structures are provided) and offer an advantageous docking member interface in terms of lateral stability as well as providing significant surface area for sturdy frictional, interlocking or other types of engagement between the members. Since the valve body will not be sutured to the docking sleeve (either an inner or outer portion thereof—as applicable) maximizing such contact, while still minimizing device size to aid in deliverability, can be important in providing a secure structure able to handle many millions of cycles of pulsing blood pressure.

Regarding the construction of the docking sleeve, its construction may substantially follow that in the '614 application for its valve bodies. Materials and assembly approaches for providing various "tri-star" and other types of docking sleeves configured as valve bodies presented in the '614 application are specifically contemplated. In some instances, the construction approaches will be modified to provide double-walled, double-cylinder or double-shelled valve docking/retention sleeves as provided herein. With such an endpoint in mind, those with skill in the art can apply the relevant teachings. Generally speaking, the valve body is polymeric, NiTi alloy (where the Af is set for superelastic or SMA use), Beta Titanium alloy, or another suitable biocompatible material or another material with a robust biocompatible coating.

However constructed, it may be desirable to utilize largely closed or uninterrupted sleeve walls to avoid inward migration of native leaflets that can damage the prosthetic leaflets. In other instances, it may be desirable to strategically locate open sections in the sleeve walls to accommodate nested inner and outer portions without overlapping material. Stated otherwise, use of nesting cylinders/shells will avoid overlap resulting in thicker wall sections that can be more difficult to manipulate into a reduce cross-section profile; or stack-up in size making fit within a percutaneous delivery system difficult.

In the latter case, overall valve system patency can be ensured by coordinating the valvular body configuration with the docking sleeve configuration so that holes provided in the outer member of the docking sleeve pair are covered or spanned when the valve body is set in place.

Figure 4A:
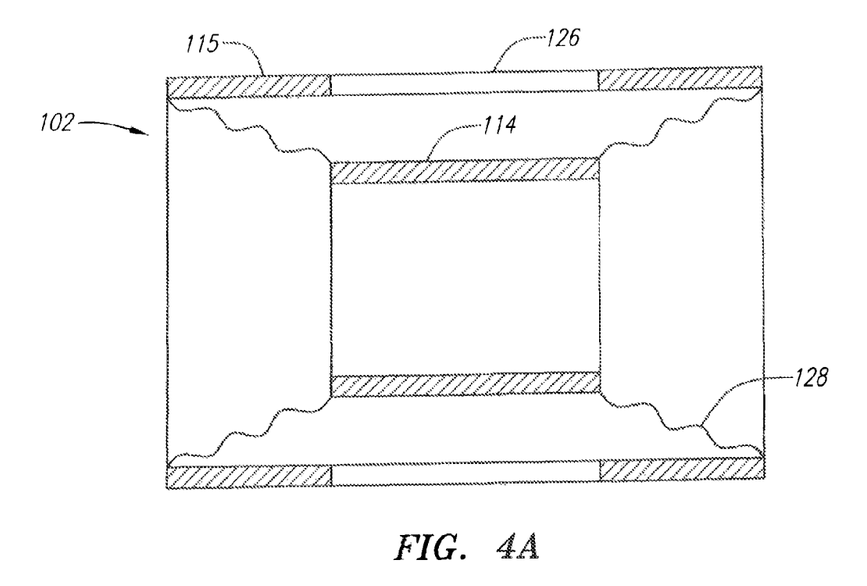
FIGS. 4A-B are axial cross-sectional and perspective views, respectively, depicting another exemplary embodiment of a docking sleeve.
Figure 4B:
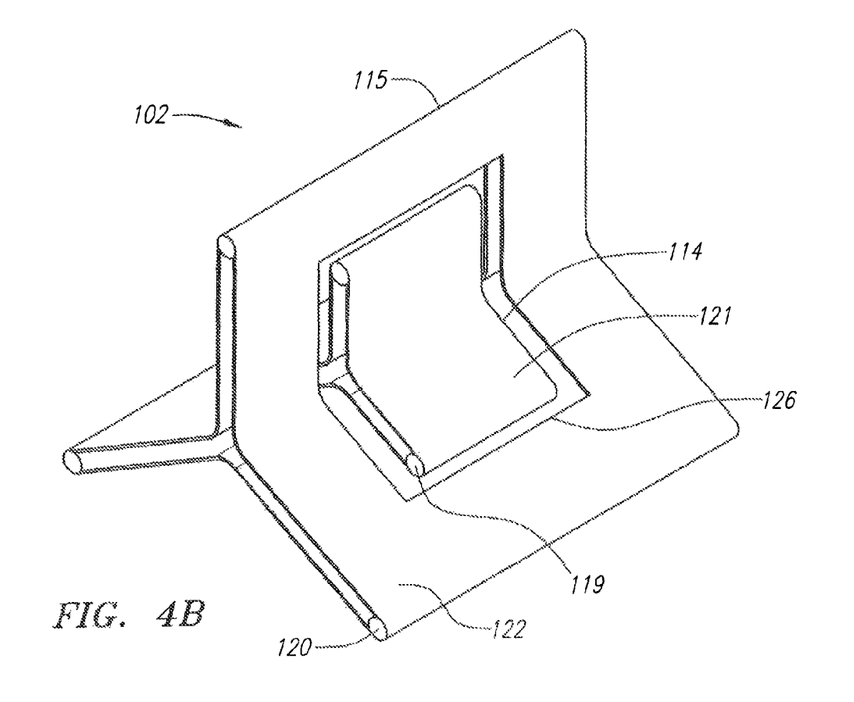

FIGS. 4A-B are axial cross-sectional and perspective views, respectively, depicting another exemplary embodiment of docking sleeve 102 having inner sleeve 114 and outer sleeve 115. FIG. 4A depicts sleeve 102 during deployment. Here, outer sleeve 115 has an aperture 126 configured to receive inner sleeve 114 (which can also be valve support structure 106). Inner sleeve 114 is coupled to outer sleeve 115 by way of a sealing device, which in this embodiment is a fabric 128. Inner sleeve 114 can be positioned within aperture 128 to prevent stack-up of the two sleeves 114 and 115 (i.e., an overlap between the sleeves 114 and 115 that increases the overall wall thickness). FIG. 4B depicts this embodiment while in the tri-star configuration. Fabric 128 is not shown.

In certain methods according to the present invention, the docking sleeve and valve body may be delivered simultaneously. Such an approach avoids the need for temporary valve approaches as described above. In yet another approach, the devices (i.e., the docking sleeve and valve member) are situated in series on a single delivery guide to allow for rapid, sequential deployment utilizing the same delivery device.

In another aspect of the method, the size of each of the prosthetic valve body and docking sleeve may be determined in various ways. Techniques described in U.S. patent application Ser. No. 11/420,189 entitled, "Assessment of Aortic Heart Valve to Facilitate Repair or Replacement," filed May 24, 2006, may be helpful in this regard. Based on such measurement, appropriately sized docking sleeve and valve bodies may be selected for a given patient from stock or an organized panel of different-sized prostheses.

Various exemplary embodiments of the invention are described below. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of the appended claims.

Any of the devices described for carrying out the subject methods may be provided in packaged combination for use in executing the method(s). These supply "kits" may further include instructions for use and be packaged in sterile trays or containers as commonly employed for such purposes.

The invention includes methods that may be performed using the subject devices. The methods may all comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally know or appreciated by those with skill in the art. For example, one with skill in the art will appreciate that a lubricious coating (e.g., hydrophilic polymers such as polyvinylpyrrolidone-based compositions, fluoropolymers such as tetrafluoroethylene, hydrophilic gel or silicones) may be used in connection with the devices, if desired, to facilitate low friction manipulation or advancement to the treatment site. The same may hold true with respect to method-based aspects of the invention in terms of additional acts as commonly or logically employed.

In addition, though the invention has been described in reference to several examples, optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in the appended claims, the singular forms "a," "an," "said," and "the" include plural referents unless the specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth n the claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of the claim language.

What is claimed is:

1. A medical apparatus, comprising:
 a prosthetic valve support structure; and
 a docking sleeve configured to interface with the support structure and configured for implantation within a blood vessel of a patient, wherein the docking sleeve comprises an inner sleeve and an outer sleeve, and wherein the docking sleeve further comprises a spring member coupled between the inner sleeve and the outer sleeve.

2. The medical apparatus of claim 1, wherein the docking sleeve comprises a tissue graft.

3. The medical apparatus of claim 1, further comprising:
 an elongate member;
 an expandable member coupled with the elongate member, the expandable member configured to deploy the docking sleeve.

4. The medical apparatus of claim 1, wherein the docking sleeve is configured to transition from an undeployed state suitable for advancement through the vasculature of a patient to a deployed state.

5. The medical apparatus of claim 1, wherein the docking sleeve is compliant.

6. The medical apparatus of claim 1, further comprising a sealing member configured to seal a space between the inner and outer sleeves.

7. The medical apparatus of claim 1, wherein at least one of the inner sleeve and the outer sleeve comprises a plurality of hinges.

8. The medical apparatus of claim 1, wherein at least one of the inner sleeve and the outer sleeve comprises a plurality of deflectable panels.

9. The medical apparatus of claim 1, wherein the outer sleeve comprises an aperture configured to receive the inner sleeve.

10. The medical apparatus of claim 1, wherein the valve support structure and docking sleeve are each configured to transition from an undeployed state suitable for advancement through the vasculature of a patient to a deployed state.

11. The medical apparatus of claim 10, wherein the docking sleeve is configured to transition from a tri-star configuration.

12. The medical apparatus of claim 1, wherein a plurality of spring members couple the outer sleeve with the inner sleeve.

13. A medical apparatus, comprising:
 a prosthetic valve support structure; and
 a docking sleeve configured to interface with the support structure and configured for implantation within a blood vessel of a patient, wherein the docking sleeve is coupled to the valve support structure by a plurality of spring members.

14. The medical apparatus of claim 13, wherein the spring members are configured to center the valve support structure.

15. The medical apparatus of claim 13, wherein the docking sleeve is configured to displace the native anatomy.

16. The medical apparatus of claim 13, wherein the docking sleeve is configured to provide a seal with the native anatomy.

17. The medical apparatus of claim 13, wherein the docking sleeve is configured to anchor against the native anatomy.

18. The medical apparatus of claim 13, wherein the docking sleeve comprises a tissue graft.

19. The medical apparatus of claim 13, wherein the docking sleeve has an inner lumen with a regular cross-sectional shape.

20. The medical apparatus of claim 13, further comprising:
 an elongate member;
 an expandable member coupled with the elongate member, the expandable member configured to deploy the docking sleeve.

21. The medical apparatus of claim 13, wherein the docking sleeve is configured to transition from an undeployed state suitable for advancement through the vasculature of a patient to a deployed state.

22. The medical apparatus of claim 13, wherein the docking sleeve is compliant.

23. The medical apparatus of claim 13, further comprising a sealing member configured to seal a space between the valve support structure and the docking sleeve.

24. The medical apparatus of claim 13, wherein the valve support structure and docking sleeve are each configured to transition from an undeployed state suitable for advancement through the vasculature of a patient to a deployed state.

25. The medical apparatus of claim 24, wherein the docking sleeve is configured to transition from a tri-star configuration.

* * * * *